US010278390B2

(12) United States Patent
Rolfe et al.

(10) Patent No.: US 10,278,390 B2
(45) Date of Patent: May 7, 2019

(54) ANTIMICROBIAL TRANSPARENT PLASTIC IN THE FORM OF FILM OR EXTRUDED SHAPE

(71) Applicants: Thomas Agnew Rolfe, Toronto (CA); Michael Christopher Nitti, Toronto (CA); Edward R Peterson, Pearland, TX (US)

(72) Inventors: Thomas Agnew Rolfe, Toronto (CA); Michael Christopher Nitti, Toronto (CA); Edward R Peterson, Pearland, TX (US)

(*) Notice: Subject to any disclaimer, the term of this patent is extended or adjusted under 35 U.S.C. 154(b) by 0 days.

(21) Appl. No.: 15/618,507

(22) Filed: Jun. 9, 2017

(65) Prior Publication Data

US 2017/0354143 A1 Dec. 14, 2017

Related U.S. Application Data

(60) Provisional application No. 62/348,025, filed on Jun. 9, 2016.

(51) Int. Cl.
| | |
|---|---|
| *A01N 33/12* | (2006.01) |
| *B32B 27/08* | (2006.01) |
| *B32B 27/30* | (2006.01) |
| *B32B 27/36* | (2006.01) |
| *C08J 5/18* | (2006.01) |
| *C09J 133/14* | (2006.01) |
| *A01N 25/10* | (2006.01) |
| *A01N 25/28* | (2006.01) |
| *A01N 25/34* | (2006.01) |
| *B32B 7/04* | (2019.01) |
| *B32B 27/18* | (2006.01) |
| *C08F 220/34* | (2006.01) |

(52) U.S. Cl.
CPC ............ *A01N 33/12* (2013.01); *A01N 25/10* (2013.01); *A01N 25/28* (2013.01); *B32B 27/08* (2013.01); *B32B 27/308* (2013.01); *B32B 27/36* (2013.01); *C08J 5/18* (2013.01); *C09J 133/14* (2013.01); *A01N 25/34* (2013.01); *B32B 7/04* (2013.01); *B32B 27/18* (2013.01); *B32B 2307/412* (2013.01); *B32B 2307/7145* (2013.01); *C08F 220/34* (2013.01)

(58) Field of Classification Search
CPC .................................. A01N 33/12; B23B 2/36
See application file for complete search history.

(56) References Cited

U.S. PATENT DOCUMENTS

| | | | | |
|---|---|---|---|---|
| 4,340,043 A * | 7/1982 | Seymour | ................. | A61L 15/44 128/849 |
| 4,775,585 A * | 10/1988 | Hagiwara | ............... | A01N 25/34 138/103 |
| 6,929,705 B2 * | 8/2005 | Myers | ..................... | A01N 25/34 106/813 |
| 8,058,324 B2 * | 11/2011 | Cebasek | .................. | C08K 3/22 523/122 |
| 2009/0130157 A1 | 5/2009 | Ylitalo et al. | | |
| 2010/0230344 A1* | 9/2010 | Srinivas | ................. | A01N 25/34 210/285 |
| 2013/0045371 A1* | 2/2013 | O'Donnell | ............... | B32B 7/02 428/215 |
| 2017/0150628 A1* | 5/2017 | Amin | .................... | C03C 21/005 |

OTHER PUBLICATIONS

Williams, "Ions, Not Particles, Make Silver Toxic to Bacteria", Current News, Jul. 11, 2012.
Kumar, et al., "Silver ion release from antimicrobial polyamide/silver composites." Biomaterials, vol. 26, Issue 14, May 2005, pp. 2081-2088.
Sankar, M. U. et al. Biopolymer-reinforced synthetic granular nanocomposites for affordable point-of-use water purification. Proc. Natl. Acad. Sci. U.S.A. 110, 8459-8464 (2013).
Kim, et al., "Antimicrobial Effect of Silver-Impregnated Cellulose: Potential for Antimicrobial Therapy", Journal of Biological Engineering, Dec. 4, 2009, 3:20.
Prabhu, et al., "Silver Nanoparticles: Mechanism of Antimicrobial Action, Synthesis, Medical Applications, and Toxicity Effects", International Nano Letters, 2012, 2:32.
Page, et al., "Antimicrobial Surfaces and Their Potential in Reducing the Role of the Inanimate Environment in the Incidence of Hospital-acquired Infections", J. Mater. Chem., 2009,19, 3819-3831.
Polivkova, et al., "Antimicrobial Treatment of Polymeric Medical Devices by Silver Nanomaterials and Related Technology", Polivkova et al., International Journal of Molecular Sciences, Feb. 15, 2017, 18, 419.
Vimala, et al., "Fabrication of Curcumin Encapsulated Chitosan-PVA Silver Nanocomposite Films for Improved Antimicrobial Activity", Journal of Biomaterials and Nanobiotechnology, 2011, 2, 55-64.

(Continued)

*Primary Examiner* — Kyle A Purdy
(74) *Attorney, Agent, or Firm* — Norton Rose Fulbright Canada LLP (57) ABSTRACT

Antimicrobial compositions and films are provided comprising a polymer and antimicrobial nanoparticles evenly dispersed in the polymer. The antimicrobial nanoparticles comprises an ionic antimicrobial agent and a support agent that localizes the ionic antimicrobial agent to surfaces of the support agent, and wherein the support agent releases the ionic antimicrobial agent through chemical exchange. In this manner, the antimicrobial nanoparticles act as a stored source of antimicrobial agents. The polymer configured to allow the ionic antimicrobial agent released by the support agent to permeate or migrate through the polymer and to the surface of the composition or film, thereby maintaining antimicrobial properties on the surface of the composition for film over an extended time.

16 Claims, 2 Drawing Sheets

(56) References Cited

OTHER PUBLICATIONS

Pabalan, et al., "Progress in Experimental Studies on the Thermodynamic and Ion Exchange Properties of Clinoptilolite", Center for Nuclear Waste Regulatory Analyses, San Antonio, Texas, Jan. 1990.

Sirelkhati, et al., "Review on Zinc Oxide Nanoparticles: Antibacterial Activity and Toxicity Mechanism", Nano-Micro Letters, vol. 7, issue 3, p. 219-242, Jul. 2015.

Kim, et al., "Antimicrobial Effects of Metal Ions (Ag+, Cu2+, Zn2+) in Hydroxyapatite", Journal of Materials Science: Materials in Medicine, vol. 9, issue 3, p. 129-134, Mar. 1998.

\* cited by examiner

ANTIMICROBIAL TRANSPARENT PLASTIC IN THE FORM OF FILM OR EXTRUDED SHAPE

CROSS-REFERENCE TO RELATED APPLICATIONS

This application claims all benefit of including priority from U.S. Provisional Application No. 62/348,025, titled "ANTIMICROBIAL TRANSPARENT PLASTIC IN THE FORM OF FILM OR EXTRUDED SHAPE" filed on Jun. 9, 2016, which is incorporated herein by reference.

FIELD OF THE INVENTION

The invention relates to the field of antimicrobial compositions and, more specifically, to antimicrobial transparent, translucent or opaque plastic materials.

BACKGROUND

Microorganisms are ubiquitous and exist on various surfaces, and through everyday routine, people come into contact with surfaces contaminated with microorganisms. Surfaces contaminated with pathogenic microorganisms can lead to the spread of diseases and infections. Frequent-contact equipment and surfaces, such as but not limited to devices with touchscreens and medical equipment, pose a serious problem due to the high frequency that people and pathogens come into contact with these devices, equipment and items. Item such as packaging and other types of containers which are required to remain relatively sterile but by the nature of their contents, their use or their location may be susceptible to colonization by pathogens also present themselves as vector points for the spread of infectious diseases to individuals or groups of individuals.

A typical method of introducing antimicrobial properties to surfaces includes applying an antimicrobial coating. However, such surface coatings are known to be susceptible to wear by abrasion, chemical attack by cleaning agents, degradation by UV aging, cuts and tears, and will deteriorate over time leading to reduction or elimination of the antimicrobial properties.

SUMMARY OF INVENTION

In one aspect, there is provided an antimicrobial composition comprising: a polymer support matrix; and antimicrobial nanoparticles evenly dispersed in the polymer support matrix, for providing a stored source of antimicrobial agents, the antimicrobial nanoparticles comprising: an ionic antimicrobial agent; and a support agent that localizes the ionic antimicrobial agent to external and/or internal surfaces of the support agent, and wherein the support agent releases the ionic antimicrobial agent through chemical exchange; wherein the polymer support matrix is cooperatively configured to allow the ionic antimicrobial agent released by the support agent to permeate or migrate through the polymer support matrix to a surface of the composition, for maintaining an effective amount of antimicrobial agent on the surface of the composition over a desired period of time to inhibit microbial growth and colonization.

In accordance with another aspect, there is provided an antimicrobial transparent film comprising: a polymer layer, comprising a polymer support matrix; and antimicrobial nanoparticles evenly dispersed in the polymer support matrix, for providing a stored source of antimicrobial agents, the antimicrobial nanoparticles comprising: an ionic antimicrobial agent; and a support agent that localizes the ionic antimicrobial agent to external and/or internal surfaces of the support agent, and wherein the support agent releases the ionic antimicrobial agent through chemical exchange; wherein the polymer support matrix is cooperatively configured to allow the ionic antimicrobial agent released by the support agent to permeate or migrate through the polymer support matrix to a surface of the film, for maintaining an effective amount of antimicrobial agent on the surface of the film over a desired period of time to inhibit microbial growth and colonization.

BRIEF DESCRIPTION OF THE FIGURES

Embodiments of the invention may best be understood by referring to the following description and accompanying drawings. In the drawings.

DETAILED DESCRIPTION

Antimicrobial plastic are useful in the manufacture of transparent antimicrobial screen protectors and other antimicrobial transparent, translucent or opaque plastic devices, for example: catheters, medical instrumentation, or re-usable medical devices. Existing screen protectors and devices have limited microbial kill rate. For example, in some cases the microbial kill rate is 99.0%, which is also referred to as 2-log microbial kill rate. However, this is insufficient for medical environments, such as hospitals and medical facilities where medical standards require 99.99% microbial kill rate, also referred to as 4-log kill rate. The 4-log microbial kill rate may also be adopted as the standard in, for example, the food services industry, educational institutions, the travel industry, financial services, the military, law enforcement and government in order to reduce the transmission of infectious diseases among and between employees and customers or in the case of military and law enforcement among and between those in service and between criminals or combatants. Existing screen protectors and frequent-contact or sterile tools, devices, surfaces or containers also do not provide long-term or persistent antimicrobial properties that meet the microbial kill rate for certain standards. These standards or agency requirements include, for example, the Environmental Protection Agency, the Federal Drug Administration, or Regulation for Registration, Evaluation, Authorization and Restriction of Chemicals (REACH), or the chemical resistance standards set by chemical producers such as Clorox™.

Furthermore, conventional screen protectors are normally based on polyethylene terephthalate (PET) which has relatively poor impact protection and inadequate clarity to meet medical and many consumer product standards. PET screen protectors typically have 10%+ haze, meaning that 10% or more of the incident light is blocked or absorbed which is inadequate for medical environments such as operating room monitors.

Deficiencies or disadvantages of existing antimicrobial products include for example: low transparency or high haze; antimicrobial coating wears off over time; high cost; low kill rate or do not meet industry standard requirements.

Antimicrobial Composition Embodiments

In one embodiment, an antimicrobial composition comprises a polymer embedded with natural or fabricated antimicrobial nanoparticles, which is configured to impart antimicrobial properties to the polymer. In some embodiments, the antimicrobial composition is transparent, translucent or opaque. In preferred embodiments, the antimicrobial composition is transparent.

As used herein, "embedded" refers to having one substances dispersed or suspended in another substance, for example by mixing. In the antimicrobial composition, the antimicrobial nanoparticles are preferably evenly dispersed in the polymer.

As used herein, "antimicrobial nanoparticles" refers to nanoparticle substances comprised of an antimicrobial agent and a support agent. As used herein, "antimicrobial agent" refers to any substance exhibiting antimicrobial properties, including but not limited to: bactericidal effects, fungicidal effects, bacteriostatic effects, and fungistatic effects. The antimicrobial agent is preferably an ionic inorganic antimicrobial agent.

As used herein, "nanoparticles" refers to particles having diameter in the range of 0.1 nm to 1000 nm. Preferably the particles are less than 500 nm, more preferably less than 300 nm, and even more preferably less than 200 nm. Most preferably, the nanoparticles are less than or equal to 100 nm in diameter.

As used herein, a "support agent" refers to a chemical substance that localizes the antimicrobial agent to external and internal surfaces of the support agent, by the. In preferred embodiments, the support agent is an adsorbent, which localizes the antimicrobial agent to the surfaces of the adsorbent by adsorption. As used herein "adsorption" refers to the adhesion of atoms, ions, or molecules of a gas or liquid or solute as a thin film on the outside surface or on internal surfaces within the material.

In addition to localizing the antimicrobial agent, the support surface also releases the antimicrobial agent through "chemical exchange". As used herein, "chemical exchange" refers to, for example, ion exchange, molecular exchange, or exchange involving water molecules. These ions or molecules interact with the support agent and occupy the surfaces spaces previously occupied by the ionic antimicrobial agents, resulting in the release of these ionic antimicrobial agents.

When the antimicrobial agent is released from the support agent by chemical exchange, the released antimicrobial agent permeates or migrates through the polymer and to a surface of the antimicrobial composition. By using a support agent that adsorbs the antimicrobial agent onto the surfaces of the support agent and releases the antimicrobial agent into the polymer, together with a polymer that allows the released antimicrobial agent to permeate or migrate through the polymer to an outer surface of the composition, the embedded antimicrobial nanoparticles provide a source of antimicrobial agents that replenishes the loss of antimicrobial agents from the outer surface of the composition through use over time. In this manner, a sufficient or effective amount of the antimicrobial agent is maintained on the surface of the composition over a desired or extended period of time to inhibit microbial growth and colonization.

This replenishment of antimicrobial agents allow the antimicrobial composition, and objects formed from the antimicrobial composition, to exhibit persistent antimicrobial properties. Since the antimicrobial agents are embedded within the polymer in the form of nanoparticles, greater efficacy over a longer period of time is achieved compared to thin antimicrobial coatings which are susceptible to rapid wear and degradation. When the antimicrobial composition is formed or extruded into a film or a shape, antimicrobial activity remains while the film or formed shape remains intact. In some embodiments, since the nanoparticles are embedded evenly throughout the composition and not just on one surface, the antimicrobial properties remains or persists even if there are surface wears or if the surface becomes abraded or scratched; whereas in the case of antimicrobial coatings, surface wears or scratches results in the loss of antimicrobial properties over time. Furthermore in some embodiments, the embedded antimicrobial nanoparticles allow for even distribution of released antimicrobial agent as the antimicrobial agent permeates or migrates through the polymer, and therefore prevents uneven surface distribution of the antimicrobial agent on the surface of the antimicrobial composition, or objects formed from the antimicrobial composition; whereas uneven distribution open results in case of coating applications.

Polymer

In some embodiments, the polymer comprises a structure, such as a matrix structure. As used herein, a "polymer matrix structure" refers to, for example, the repeating structural unit of the polymer, which may include cross-linking. The polymer is configured such that the antimicrobial ions, such as $Ag+$ ions, are able to freely permeate or migrate through the polymer and to the surface of the composition to maintain or achieve a sufficient or effective amount of the antimicrobial agent on the surface of the composition. In preferred embodiments, the polymer comprises spaces or pathways that are of sufficient size to allow the ionic metal particles to migrate or pass through to the surface of the composition. In further embodiments, the polymer may comprise charged groups or partially charged groups in the spaces or pathways to offer migrating ions a stabilizing structure for the ions to move through the body of the polymer. In other embodiments, the polymer comprises a chemical gradient or a chemical potential gradient to drive the migration of the ionic antimicrobial agents.

Polymers having low crystallinity and high quality, and also lacking impurities which may reflect or absorb light are preferred. For example, polymers are selected for use in the antimicrobial composition based low crystallinity, appropriate density, presence or absence of charged functional groups, chain length, and/or branch structure. For example, using polymers having less than 75% crystallinity, less than 50% crystallinity, less than 25% crystallinity, less than 10% crystallinity, less than 5% crystallinity, less than 3% crystallinity, less than 2% crystallinity, less than 1% crystallinity, or less than 0.5% crystallinity.

Examples of polymers include, but are not limited to: acrylic polymer, polyolefin polymer, thermoplastic synthetic polymers, polypropylene, polypropylene, polyethylene terephthalate, acetate polymers, polystyrene, polyvinyl chloride, polyvinylidene chloride, polyamides, polyacetals, polyesters, polyvinyl alcohols, carbonate polymers, butyrate polymer, halogenated polymer, polyether polymer, styrene butadiene polymer, polyurethanes, ABS resins, acrylic resins, fluorine-containing resins, polyurethane elastomers, or polyester elastomers.

In one preferred embodiment, the polymer support matrix comprises an urethane polymer, and in more preferred embodiments the polymer comprises thermoplastic polyurethanes (TPU). In a preferred embodiment for a transparent antimicrobial composition, the polymer is a polycaprolactone based aliphatic TPU resin. In some embodiment, the TPU polymer has a shore hardness 60 D.

In another embodiment, the polymer comprises an acrylic polymer. In yet another preferred embodiment, the polymer comprises an acrylic layer bonded to a TPU layer.

As used herein, "shore hardness" refers to a measure of hardness of a material, which is quantified using a durometer scale. Shore hardness specifications may vary greatly depending on application. In some embodiments, the polymer has a shore hardness of greater than 20 D, more preferably greater than 30 D, even more preferably greater than 40 D. In a preferred embodiment, the hardness is 60 D or 70 D. Other hardness scales are also available and a person of skill in the art is able to convert between different scales. For example, in some embodiments the polymer has a shore hardness of 75 A to 100 A. In embodiments where the polymer is TPU, shore hardness of A 65 to D 70 is preferred. In embodiments where an acrylic layer is bonded to a TPU layer, a higher range on the D scale is preferred.

Advantages of using a polycaprolactone TPU include, but a not limited to, inherent toughness, low-temperature performance, and a relatively high resistance to hydrolysis. Aliphatic TPUs based on isocyanates, such as, H12 MDI, HDI and IPDI are light, stable and offer excellent optical clarity.

In other embodiments, the polymer support matrix is comprised of an ABS (Acrylonitrile butadiene styrene), for example, CoolPoly®, Terblend, Absylux®, ABS-FR Acrylonitrile butadiene styrene polyvinyl chloride blend, or conductive ABS; Kydex (acrylic polyvinyl chloride polymer); Noryl (blend of polyphenylene oxide and styrene); PETG (Polyethylene Terephthalate Glycol); or High Impact polystyrene. In other embodiments, the polymer is Lexan (polycarbonate), PETG (glycol modified polyethylene teraphthalate), or polycaprolactam polyurethane.

In other embodiments, the polymer is a thermosetting synthetic polymers such as phenolic resins, urea resins and urethane resins; or regenerated or semi-synthetic polymers such as rayon, cuprammonium rayon, acetate rayon and triacetate rayon.

Surprisingly, the antimicrobial agent released from antimicrobial nanoparticles embedded in the above listed polymers are able to migrate or permeate through the polymer to the surface of the composition, to replenish antimicrobial agents lost from the surface of the composition through use and wear and thereby allows the composition to exhibit antimicrobial efficacy over extended period of time. Some advantageous properties of the above listed polymers include low haze but improved tactile acceptability, specific chemical resistance, reduced UV degradation, reduced age related crystallization, and improved impact absorption.

Antimicrobial Agent

A number of inorganic antimicrobial agents exhibit antimicrobial properties (see Example section below). In one embodiment, the antimicrobial agents are preferably inorganic antimicrobial agents and include, but are not limited to, Aluminum, Antimony, Barium, Bismuth, Copper, Gold, Lead, Nickel, Silver, Tellurium, Thallium, Tin and Zinc alone or in combination. In preferred embodiments, the inorganic antimicrobial agent comprises silver, zinc, gold, copper, aluminum. In even more preferred embodiments, the inorganic antimicrobial agent comprises silver and zinc together or separately.

Silver-containing nanoparticles exhibit antimicrobial properties. In order for silver to have any antimicrobial properties, it must be in its ionized form. For example, silver in its non-ionized form is inert, but contact with moisture leads to the release of silver ions. The same is true of other inorganic antimicrobial agents, for example, $Cu^{2+}$ or $Zn^{2+}$ which exhibit antimicrobial properties. As used herein, an "inorganic antimicrobial agents" refers to ionized forms of the antimicrobial agents which exhibit antimicrobial properties.

Inorganic antimicrobial agents are more effective in nanoparticle size. Furthermore, the shape of the nanoparticles can also impact its antimicrobial effects. For example in the case of $AgNO_3$, triangular nanoparticles exhibit greater antimicrobial activity than spherical or rod-shaped nanoparticles.

In one embodiment, the antimicrobial nanoparticles are at most 100 nm in size; more preferably 5-100 nm; more preferably 5-25 nm; more preferably 5-10 nm; preferably 7-10 nm; more preferably about 7 nm. In other embodiments, the nanoparticles are triangular, spherical, rod-shaped, trilobed, hollow cylinder; more preferably triangular in shape.

The antimicrobials nanoparticles are embedded into the polymer at the time of manufacture in sufficient density and uniform distribution so as to achieve a desired amount of antimicrobial agent release over time. This in turn maintains a sufficient or effective amount of antimicrobial agent on the surface of objects formed from the composition. In some embodiments, the concentration of antimicrobial nanoparticles embedded in the polymer such is least 15 PPB or at least 10 PPMw. In preferred embodiments, the concentration is at least 30 PPMw. In most preferred embodiments, the concentration is at least 50 PPMw.

In some embodiments, the antimicrobial composition has an effective amount of antimicrobial agent maintained on the surface of the antimicrobial composition to exhibit 2-log (99%) microbial kill-rate persistently or over an extended period of time. In other preferred embodiments, the antimicrobial composition has an effective amount of antimicrobial agent maintained on the surface of the antimicrobial composition to exhibit 3-log (99.9%) microbial kill-rate persistently or over an extended period of time. In most preferred embodiments, the antimicrobial composition has an effective amount of antimicrobial agent maintained on the surface of the antimicrobial composition to exhibit 4-log (99.99%) microbial kill-rate persistently or over an extended period of time.

Support Agent

For inorganic antimicrobial agents, such as silver, to exhibit antimicrobial properties, they must be in an ionic form. In some embodiments, the support agent comprises partially charged functional groups to localize the antimicrobial agent. For example, the support agent may have exposed oxygen atoms that impart a partially negative charge to the oxygen atom.

In some embodiments, the support agent holds onto the inorganic antimicrobial ions and gradually releases the inorganic antimicrobial ions into the polymer support matrix. In some embodiments, the support agent releases the inorganic antimicrobial ions in the presence of water molecules through molecule or ion exchange. In some embodiments, the support agent gradually or persistently releases the inorganic antimicrobial ions with a half-life of 1 year, 2 years, 3 years, or 5 years. More preferably, the half-life is 10 years, 15 years, or 20 years. Most preferably, the half-life is 30 years or 40 years.

Examples of support agents include various inorganic or organic microporous adsorbent material. For example, pure aluminas of varying density and porosity, natural clays like montmorillinite and manufactured silicates that contain various anions and cations with varying properties, metal oxides, and metal silicates such as natural talc. Organic ion support materials include but are not limited to: polymethylmethacrylates, polyacrylamide copolymer, ethylene maleic anhydride copolymer, cross-linked carboxymethylcellulose, polyvinyl alcohol copolymers, cross-linked polyethylene oxide, and starch grafted copolymer of polyacrylonitrile commonly classed as superabsorbent polymers. Additional ion support materials include sulfonated polystyrene in particular and ion exchange resins in general. Other manufactured inorganic support materials include various pure and mixed homogeneous and structured or layered silicates, oxides, carbides, carbonates. In some instances these may contain compounded or pure forms of titanium, zinc, iron, chromium, nickel, cobalt or mixtures thereof, pure carbon, and metallic platinum, palladium silver and gold. In preferred embodiments, a support agent is selected that is capable of adhering and subsequently releasing antimicrobial ions for replenishing the antimicrobial agent within the polymer structure and migrating persistently to the surface is suitable for providing a source of the active antimicrobial agent.

In one preferred embodiment, the support agent is a zeolite microporous aluminosilicate mineral. Zeolite is a porous matrix of sodium aluminosilicate which binds a large amount of ions, such as silver ions, on the interior surfaces of zeolite micropores and throughout the external surfaces. In preferred embodiments, the pores of the zeolite are 300 to 1200 picometers. In more preferred embodiments, the pore sizes are 300 to 500 picometers. Zeolites have large vacant spaces or pores in their structures that allow space for large cations. In some embodiments, the pores are interconnected and form long wide channels of varying sizes depending on the mineral. These channels allow for the movement of resident ions and molecules into and out of the structure.

Zeolites have a framework silicates consisting of interlocking tetrahedrons of $SiO_4$ and $AlO_4$. The aluminum atom adds a negatively charged group to the zeolite structure, which allows the zeolite to bind to cations, such as Ag+. Therefore, zeolites having higher aluminum to silica ratio results in higher overall full or partial negative charges, which in turn allows the zeolite to bind to more cations, such as Ag+. In one preferred embodiment wherein the support agent is zeolite microporous aluminosilicate mineral, the zeolite has an aluminum to silica ratio of at least 3, at least 5, at least 10, at least 15, at least 20, or at least 25. In preferred embodiments, the aluminum to silica ratio is at least 10, at least 15, or at least 20. In one preferred embodiment, the aluminum to silica ratio is at least 14.

Appropriate support agent depends at least in part on the inorganic antimicrobial agent used. A person of skill in the art is able to identify compatible support agent given an inorganic antimicrobial agent.

In one embodiment, the inorganic antimicrobial agent comprises is encapsulated in glass as nanoparticles. In preferred embodiments, the inorganic antimicrobial agent comprises glass encapsulated ionic silver nano-particles. One example glass encapsulation is available from Wako Pure Chemical Ind., Osaka, Japan or NanoSeedz™.

Film Embodiments

In alternate embodiments, the antimicrobial composition is formed into an antimicrobial transparent film or sheet. Antimicrobial films are useful in imparting antimicrobial properties to surfaces, such as display screens, touchscreens, monitors, video screens, windows, doors, or other surfaces to be protected. In preferred embodiments, a transparent antimicrobial composition is used to form antimicrobial films.

As used herein, "transparent" means allowing sufficient light to pass through. In one embodiment, an antimicrobial transparent film or sheet typically has less than 10% haze. In preferred embodiments, there is less than 7% haze. In most preferred embodiments, there is less than 5% haze. One example of measuring haze is using the ASTM D1003 standard test method for haze and luminous transmittance of transparent plastics, so that objects behind can be distinctly seen. High level of transparency is preferred, for example, for film applications, screen protectors or masks. On the other hand, a lower level of transparency is sufficient in embodiments where the antimicrobial composition is extruded or formed for manufacture of products such as medical catheters, packaging, wound dressings, tubes, curtains, tools or gloves. In order to maintain transparency, the antimicrobial composition comprises a polymer that has low impurities.

In one embodiment, an antimicrobial composition comprises a thermoplastic urethane polymer. In preferred embodiments, an antimicrobial composition comprises a polycaprolactone based aliphatic TPU resin, in order to retain high transparency. Urethane polymer (TPU) are low in impurities which maintains highs transparency. In another preferred embodiment, the polymer comprises an acrylic polymer embedded with the antimicrobial nanoparticles. In yet another preferred embodiment, the polymer comprises a top acrylic layer embedded with the antimicrobial nanoparticles, and this acrylic top layer is bonded to a TPU layer, which is optionally also embedded with antimicrobial nanoparticles.

The antimicrobial nanoparticles are very small and exhibit good antimicrobial activity because of their high surface area to volume, and they also maintain a high level of transparency in a TPU or acrylic film. The smaller the nanoparticles, the weaker their potential for scattering of visible light, hence improving the film's overall light transmission. Also, if the particle size is too large, then the surface of the film becomes bumpy, which is highly undesirable in a touchscreen application due to poor tactile acceptance. A bumpy surface can also lead to locations on the film that allow microbes to adhere.

Surprisingly, the presence of the antimicrobial agent in the antimicrobial composition does not significantly inhibit the passage of light through an antimicrobial film when the antimicrobial agent nanoparticles have a diameter of less than 100 nm. Preferably, the size of the nanoparticles are less than a quarter of the wavelength of visible length. In one embodiment of a transparent antimicrobial film, the nanoparticles are at most 100 nm in size; more preferably 5-100 nm; more preferably 5-25 nm; more preferably 5-10 nm; more preferably 7-10 nm; more preferably about 7 nm.

The density or concentration of the nanoparticles embedded in the polymer support matrix can also affect the transparency of the film. In some embodiments, any two nanoparticles are separated by a distance of at least twice the diameter of the nanoparticles. In other embodiments, any two nanoparticles are separated by a distance of at least 3 times, 5 times, 8 times, 10 times, 15 times, 20 times, 50 times, or 100 times the diameter of the nanoparticles. For nanoparticles having a diameter of about 100 nm, it is preferred that any two nanoparticles are separated by a distance of at least 8 times the diameter. For smaller nanoparticles, for example nanoparticles with a diameter of about 10 nm, it is preferred that any two nanoparticles are separated by a distance of at least twice the diameter.

In other embodiments, the antimicrobial transparent composition is formed into an antimicrobial transparent film or sheet that re-directs light so as to create a bi-directional or multi-directional privacy screen.

In one embodiment, an antimicrobial transparent film maintains capacitance when applied to, for example, capacitive displays or touchscreens. When a finger, which is electrically conductive, or conductive stylus contacts a touchscreen, an electrical charge is transferred to the finger to complete a circuit, creating a voltage drop at that point of contact with the touchscreen. The location of voltage drop is processed by a processor to create an interactive touchscreen display. Given the presence of ionic antimicrobial agents or nanoparticles in the polymer, non-interference with capacitance touchscreens is one factor in selecting appropriate antimicrobial agents or nanoparticles for an antimicrobial film. Non-interference with light as in the case of Frustrated Total Internal Reflection FTIR based functional screens is also important in the selection of appropriate nanoparticles for the film.

Capacitance is the ability to store and concentrate an electrical field within a material. Non-metals are non-conductors and thereby have a resistance to electrical transmission. Capacitance is the measure or quantization of this resistance. Different polymers have differing intrinsic capacitance, normally given as capacitance per millimeter, and therefore the actual working capacitance is altered in some embodiments by changing the thickness of a film layer, or in other embodiments, introducing one or more of layers to the film. Polymer additives can be added to raise capacitance values although these will generally impart reduced transparency at higher concentrations. In general, capacitance increases as the prevalence of hetero atoms increases and crystallinity decreases. Examples of ways to alter the actual capacitance of a film structure is found, for example, in U.S. Pat. No. 5,250,587, the entire disclosure of which is hereby incorporated by reference.

The capacitance of a film is influenced by a number of factors, for example, the density of inorganic material present in the film, thickness of the film, composition of the film, the presence of oxygen and nitrogen groups in the TPU, as well as the presence of fillers. Furthermore different touchscreens have different capacitance requirements tailored to the applied functions of each touchscreen. A person skilled in the art is able to identify and select the necessary combination of factors, such as from above, to manufacture a film having the desired capacitance based on the requirements of the touchscreen and its function.

The polymer is the active modality for rendering active and correct capacitance and light transmission, which is something the antimicrobial agent could not do. It is the combination that renders a new form of matter for the specific use in a new invention.

In some embodiments, an antimicrobial transparent film can be applied to a substrate surface to impart antimicrobial properties to the substrate surface by transfer of antimicrobial agent from a contact surface of the antimicrobial transparent film to the substrate surface.

In some embodiments, the antimicrobial transparent film is applied to surfaces with adhesives. Example adhesives include, but are not limited to, silicone adhesives, acrylic adhesive, or reactive adhesives. As used herein, reactive adhesives refers to adhesives that undergo a chemical reaction that reacts with both the film and substrate surfaces and form a chemical bonds between them. In one embodiment, the adhesive comprises sodium silicate. In some embodiments, the adhesive layer comprises a dry-apply and in another embodiment wet-apply adhesive. An alcohol based solution may be used on the adhesive and/or a surface on which an antimicrobial firm is to be applied. This application of alcohol allows for easy, sterile and accurate positioning of the film on the screen. In yet other embodiments, an adhesive is applied to the film and protected by a peel back film layer. Other examples of adhesion surfaces and adhesives are known, and will vary with the surface to which the antimicrobial film is applied as well as the polymer used. Smoothness of the surface, the complexity of the surface and the adhesion requirements are factors in selecting an appropriate adhesive. In some cases, a contact adherent will be a solution comprising water, ammonia and organic alcohol that is non-permanent and allows easy removal of the film as well as easy application.

In some embodiments the adhesive layer is non-permanent and renders the film easily detachable, or in other embodiments the adhesive layer chemically reacts with a substrate surface render the film non-removable.

Antimicrobial sheets are useful in manufacturing, for example, tape, packaging, or covers.

For optimal transparency and capacitive functionality, the antimicrobial composition be formed into a film having a thickness up to 0.01 or 0.005 inch. More preferably, the film is less than 0.007 inch in thickness. Most preferably, the film between 0.001 and 0.005 inch in thickness. In one preferred embodiment, the film is about 0.005 inch in thickness. Even more preferably, the film is 0.002 to 0.003 inches in thickness. In embodiments where the antimicrobial composition is formed into flat sheets, the thickness is 0.006 to 0.1 inch. In other embodiments, a sheet of greater thickness is preferred for resilient sheets, for example for use in making face shields.

In some embodiments additives are added to produce desired colour. For example, the antimicrobial composition is transparent but pigment is added to add colour to the composition. In some embodiments additives impart color, or alter the way light is reflected, refracted or transmitted through the antimicrobial composition depending on the additive, its concentration and its particle size. Such additive properties are known in the art.

Multilayer Film Embodiments

In one embodiment, an antimicrobial transparent composition is formed or coextruded into multilayer films. These multilayer films comprise one or more antimicrobial layer comprising a polymer embedded with an antimicrobial agent in the form of nanoparticles. Additional layers are added below the antimicrobial layer for added function to the multilayer film, while preserving the antimicrobial properties of the multilayer film. Examples of additional layers include, but are not limited to: polymer layer for shock or energy absorption and strength, rigidity layer, light filter layer, UV degradation resistant layer, water barrier layer, privacy filter layer, oxygen barrier layer, opacity layer, vision enhancing layer, chemical resistant layer, a photosensitive layer containing light-sensitive polychromatic molecules, embedded sensor layer or combinations thereof. In some embodiments, these additional layers are also embedded with nanoparticle antimicrobial agents. The additional layers impart added resistance, rigidity, light polarization, capacitance, conductivity or other electronic or optical properties. Polycarbonates may also be used to produce these added feature layers.

A water barrier layer is advantages for maintaining water repellency. An oxygen barrier lay is advantageous for keeping electronics from oxidizing when they run hot or are designed to run best under an oxygen deficient atmosphere and may be blanketed with a non-reacting gas such as Xenon or argon. Bi-refringent layers set at an angle to one another would reduce the ability of reading the screen except when viewed directly on. Polymers may also be selected based on their ability, for example, to stretch, bend, deform, resist crystallization and aging, alter photosensitivity, or accept or resist shear deformation.

The multiple layers are attached each other with adhesives, using the same or different adhesive for each layer. The presence of multiple layers adds rigidity and strength to the film and also results in surprisingly increased energy absorption and impact protection for screens, monitors and touchscreens. In some embodiments, the film comprises 2 to 7 layers. In preferred embodiments, the film comprises 2 to 5 layers. In some preferred embodiments, the film comprises 3 layers. The number of layers are dependent on the desired application and the attributes a film requires to fulfill its desired function. Total combined thickness may be limited for reasons of maintaining capacitance (such as in touchscreen operation), preventing vision distortion, and maintaining transparency in certain applications.

Figure 1:
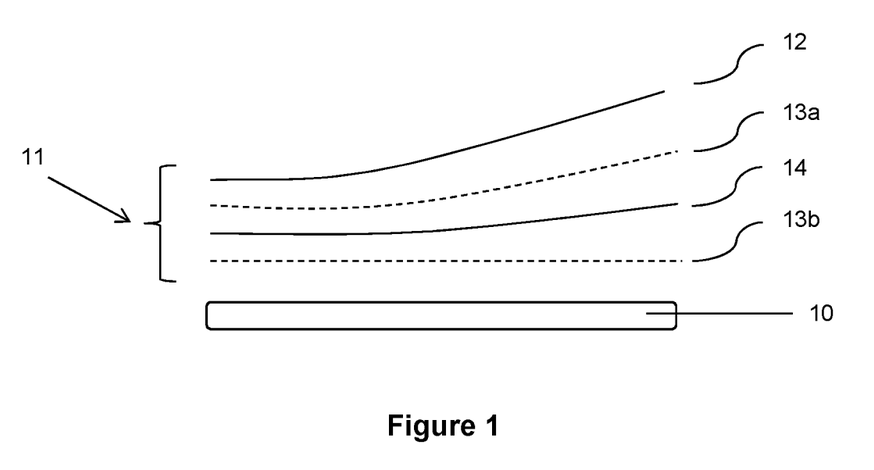
FIG. 1 shows a first embodiment of an antimicrobial multilayered film.

A first embodiment of a multilayer antimicrobial film 11 is shown in FIG. 1, applied to a surface 10, such as a passive or interactive display surface. A top transparent layer 12 comprises a polymer embedded with an antimicrobial agent in the form of nanoparticles. This top layer imparts antimicrobial properties to the overall film by providing an antimicrobial outer surface. A bottom transparent polymer layer 14 is provided comprising a transparent polymer for energy or shock absorption and for providing strength to the film 11. Alternatively, the bottom transparent polymer layer 14, is a transparent polymer with nanoparticle antimicrobial agent embedded, that is the same or different from the top transparent layer. A first adhesive layer 13a is provided between top transparent layer 12 and bottom transparent layer 14 to bind these two layers together. A second adhesive layer 13b is provided for applying the multilayer antimicrobial film 11 to the substrate 10. The first and second adhesive layers may comprise the same or different adhesive.

Figure 2:
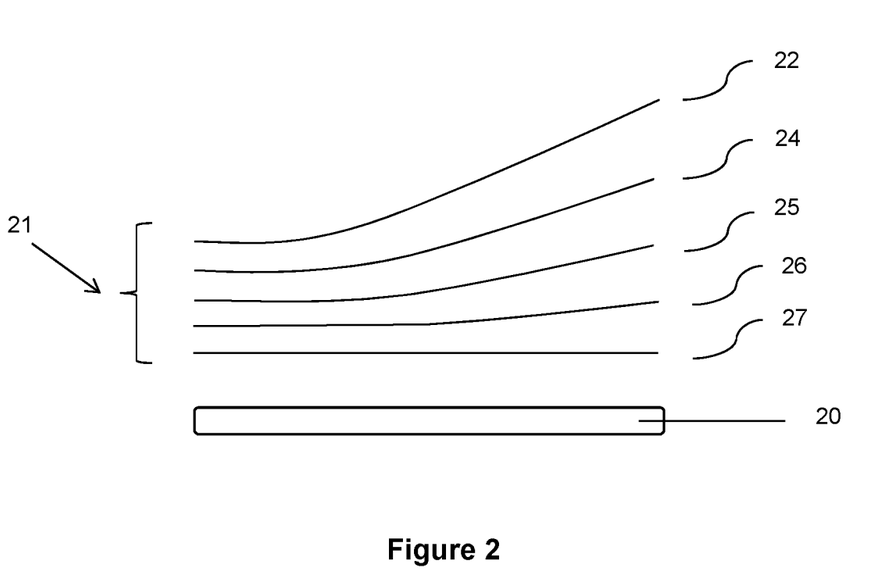
FIG. 2 shows a second embodiment of an antimicrobial multilayered film.

A second embodiment of a multilayer antimicrobial film 21 is shown in FIG. 2, applied to a surface 20, such as a passive or interactive display surface. In this embodiment, the top layer 22 comprises a polymer embedded with an antimicrobial agent in the form of nanoparticles. This top layer is further treated with a porous surface treatment that provides glare, oil, abrasion, or water resistance. Second layer 24 is a UV degradation resistant layer. Third layer 25 is a privacy layer that decreases the viewing angle of a screen or display to which the film is applied, thereby preventing the screen or display from being viewed from the side. Fourth layer 26 is rigidity layer comprising a polymer of higher density or hardness to increase overall rigidity of the film 21. The bottom layer 27 is a water barrier layer for preventing the penetration of water through the film and onto the screen or display. Adhesive layers (not shown) between the top, second, third, fourth, and fifth layer binds these layers together.

Figure 3:
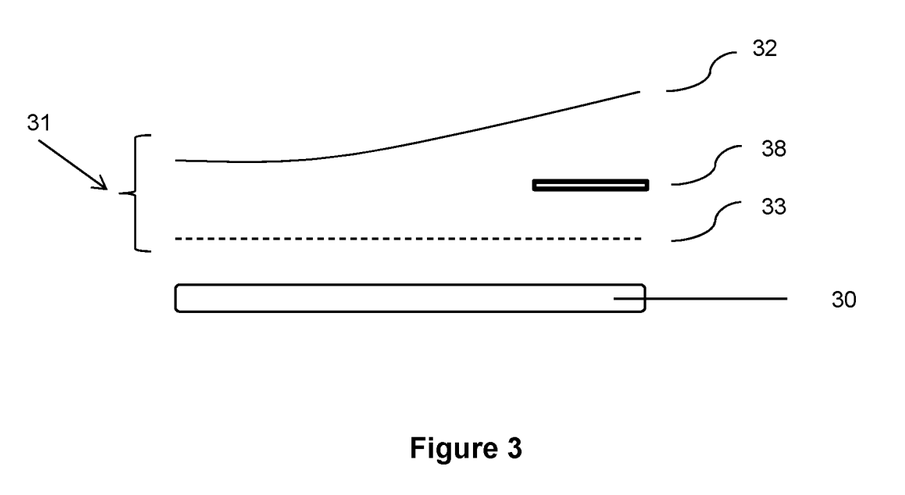
FIG. 3 shows a third embodiment of an antimicrobial multilayered film.

A third embodiment of a multilayer antimicrobial film 31 is shown in FIG. 3, embedded with one or more electronic or optical component 38 for supporting touchscreen function or other sensor functions. Examples of electronic or optical components include, but are not limited to, capacitance measuring addressable electrodes, light or electrical conductive substances, RFID chips, fingerprint/pattern identification sensors, or biological sensors. Examples of biological sensors include, but are not limited to, temperature sensors, blood pressure sensors, or metabolic measurement sensors. In this embodiment, the film 31 is applied to a substrate 30 such as a touchscreen in cases where the electronic or optical component 38 is, for example, a RFID chip, or the film 31 is applied to a body surface where the electronic or optical component 38 is, for example, a biological sensor. A top transparent layer 32 comprises a polymer embedded with an antimicrobial agent in the form of nanoparticles, which applied to the substrate 30 with an adhesive layer 33. An electronic or optical component 38 is embedded in film 31 between top transparent layer 32 and adhesive layer 33.

In this embodiment, the embedded antimicrobial agent is persistent and fully functional and the inclusion of electronic or optical components do not restrict light transmission or functionality any more than if they were embedded in a substructure beneath the antimicrobial film. An electronic or optical component may also be embedded in an antimicrobial composition that has been extruded into a structure for use in manufacture of devices, examples of which include but are not limited to electrode patches, body wraps, partial body wraps, socks, body side surfaces of casts, or gloves. In this extruded form, the placement of sensors on or within the antimicrobial film or device may create greater monitoring accuracy through redundancy and less need for accurate placement of sensors.

Figure 4:
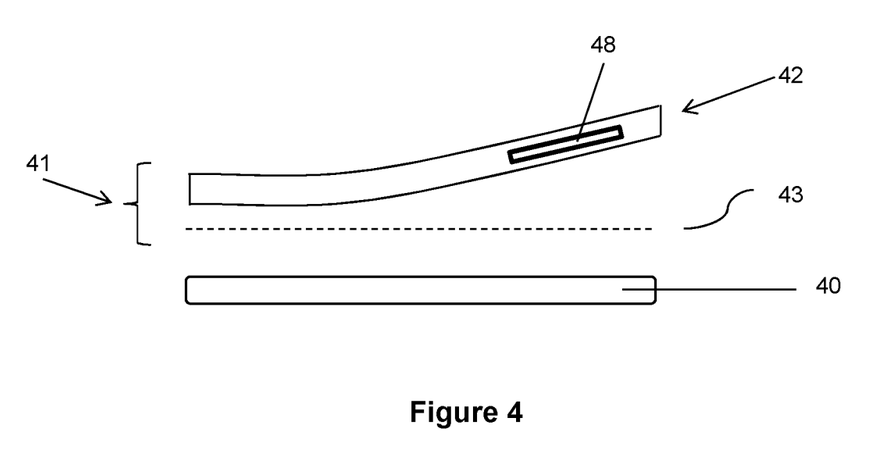
FIG. 4 shows a fourth embodiment of an antimicrobial multilayered film.

A fourth embodiment of multilayer antimicrobial film 41 is shown in FIG. 4. A top transparent layer 42 comprises a polymer embedded with an antimicrobial agent in the form of nanoparticles. In this embodiment, one or more electronic or optical component 48 is embedded in the polymer of top transparent layer 48. Film 41 further comprises an adhesive layer 43, for application of film 41 onto substrate 40.

In one embodiment, an Ultra Violet (UV) light sensor together with an RFID chip are embedded within a antimicrobial film which is then placed onto the surface of a monitor, screen or touchscreen. Since UV light is freely able to pass through the antimicrobial transparent film, UV light can be used as an initial sterilization method and the antimicrobial properties of the film maintains sterility thereafter. Such applications are useful in meeting healthcare rapid sterilization assurance protocols while maintaining antimicrobial activity for the entire surface of a device.

Formed Structure Embodiments

In some embodiments, this composition is extruded, molded, or formed into various shapes and structures for use in the manufacturing of transparent, translucent or opaque objects or devices that exhibit persistent surface antimicrobial properties. For example, the antimicrobial composition can be used to make antimicrobial face masks, tubing, inhalers, curtains and drapes, gloves, tools, medical equipment, dispensers, aprons, containers, catheters or transparent or translucent wound dressings or biometric monitors as well as many other objects benefiting from persistent antimicrobial surface activity.

In some embodiments additives are added to produce desired translucency, opacity or colour. For example, the antimicrobial composition is transparent but pigment is added to add colour to the composition. In some embodiments additives impart color, while in other embodiments additives do not impart colour, or alter the way light is reflected, refracted or transmitted through the antimicrobial composition depending on the additive, its concentration and its particle size. Such additive properties are known in the art.

Objects made from the antimicrobial composition or the antimicrobial transparent film are useful in settings, such as but not limited to, hospitals, medical and health care facilities, research and lab facilities other pathogen contaminated areas and veterinary settings where prevention of microorganism contamination and/or spreading of pathogens is desired. One high level uses are public places where pathogens may be transferred from one person or creature or other microbe vector to another on surfaces in the private or public domain. High potential surfaces include those touched by infected persons or animals. Even higher potential surfaces include those such as catheters, wound dressings, touch-screens, and video monitors which have and maintain a warm temperature and thus promote or incubate the growth of pathogens. Environments with moderate to high levels of humidity within the environments above enhance the long term biological viability and resulting infectiousness. Wherever a touchscreen or transparent surface is used by more than one person—for example, tenant listings in building lobbies, bank ATMs, screens in the Food Services industry from restaurants to production plants, touchscreens in the education sectors such as tablets in the classroom etc.—there is a risk that pathogens or microorganisms may be transferred.

Manufacture

In one aspect, the antimicrobial transparent or translucent film is manufactured by: mixing the a polymer with antimicrobial nanoparticles for embedding the nanoparticles in the polymer; extruding, coextruding, laying down or forming the polymer; and applying an adhesive coating to the extruded polymer. In some embodiments, the step of applying the adhesive layer or coating comprises mechanical adhesion, chemical adhesion, reactive adhesion, dispersive adhesion, electrostatic adhesion, or diffusive adhesion.

In one embodiment, a method of manufacturing an antimicrobial composition or film comprises the steps of: mixing a polymer with antimicrobial nanoparticles for embedding the nanoparticles uniformly throughout the polymer; extruding, forming or laying down the polymer in a single or reactively bonded multilayer film.

In some embodiments, a multilayered film is fabricated by methods involving extrusion, loss of solvent, reactive forming, pressure forming, and other known methods of forming a layered or non-layered three dimensional structure which may have a uniform or non-uniform cross-section.

In some embodiments, the method comprises applying an adhesive coating or reactive bonding agent to the polymer coincident with or subsequent to extrusion, forming or laying down. In preferred embodiments, the method further comprises bonding one or more additional layers onto the antimicrobial layer, in order to impart strength to the film.

In some embodiments, the method further comprises creating an optional porous surface treatment.

As used herein, in chemical adhesion, two materials may form a compound at the joint. The strongest joints are where atoms of the two materials swap or share electrons (known as ionic bonding or covalent bonding, respectively). Chemical adhesion occurs when the surface atoms of two separate surfaces form ionic, covalent, or hydrogen bonds.

As used herein, in dispersive adhesion, also known as physisorption, two materials are held together by van der Waals forces. In the simple cases, such molecules are therefore non-polar with respect to average charge density, although in larger or more complex molecules, there may be multiple "poles" or regions of greater partial positive or negative charge.

As used herein, in electrostatic adhesion, some non-conducting materials may pass electrons to form a difference in electrical charge at the join. This results in a structure similar to a capacitor and creates an attractive electrostatic force between the materials.

As used herein, in diffusive adhesion some materials may merge at the joint by diffusion. This may occur when the molecules of both materials are mobile and soluble in each other. This would be particularly effective with polymer chains where one end of the molecule diffuses into the other material.

In some embodiments, an antimicrobial transparent film is manufactured by applying an adhesive layer to a polymer layer by mechanical adhesion, chemical adhesion, dispersive adhesion, electrostatic adhesion, reactive adhesion or diffusive adhesion.

In some embodiments, an antimicrobial multilayered film is manufactured by bonding one or more additional layers and the polymer layer bonded together by contact adhesion, melt adhesion, reactive adhesion, cold pressing, ultrasonic sealing, or thermal sealing.

The following examples are illustrative of various aspects of the invention, and do not limit the broad aspects of the invention as disclosed herein.

EXAMPLES

The metals listed below all show increased efficacy in nano-partical size.

Aluminium: Aluminium acetate (Burow's solution) is a mild astringent mild antiseptic. Aluminium-based antiperspirant ingredients ("aluminum salts") such as aluminum chlorohydrate, activated aluminum chlorohydrates, and aluminum-zirconium-glycine (AZG) complexes work by forming superficial plugs in the sweat ducts, reducing the flow of perspiration.

Antimony: Orthoesters of diarylstibinic acids are components of fungicides and bactericides, used in paints, plastics, and fibers. Trivalent organic antimony was used in therapy for schistosomiasis.

Barium: Barium polysulfide is a fungicide and acaricide that has been used in fruit and grape growing.

Bismuth: Bismuth compounds exhibit astringent, antiphlogistic, bacteriostatic, and disinfecting effects. For example, bismuth subgallate is an antimycotics.

Copper: Small amounts of copper ions in water are bactericidal. Copper sulfate mixed with lime is a fungicide and antihelminthic. Copper sulfate can destroy green algae (algicide) that grow in reservoirs, stock ponds, swimming pools, and fish tanks. Copper 8-hydroxyquinoline can be added to paint to prevent mildew.

Gold: Gold inhibits the growth of bacteria.

Lead: Lead arsenate is insecticidal herbicidal. Thiomethyltriphenyllead is an antifungal agent, a rodent repellant, and a preservative. Tributyllead acetate and tributylleadimidazoleas are also preservatives.

Nickel: Nickel exhibit toxicity to bacteria, yeasts, and fungi.

Silver: The metabolism of bacteria is adversely affected by silver ions at concentrations of 0.01-0.1 mg/L. Therefore, even less soluble silver compounds, such as silver chloride, also act as bactericides or germicides, but not the much less soluble silver sulfide. In the presence of atmospheric oxygen, metallic silver also has a bactericidal effect due to the formation of silver oxide, which is soluble enough to cause it to form some ions. Bactericidal concentrations are produced rapidly by adding colloidal silver, which has a high surface area. Even objects with a solid silver surface (e.g., table silver, silver coins, or silver foil) have a bactericidal effect. Silver sulfadiazine is an antiseptic. An equilibrium dispersion of colloidal silver with dissolved silver ions can be used to purify drinking water at sea. Surfacine (silver iodide) is a antimicrobial for application to surfaces. In some cases, silver-impregnated wound dressings are useful against antibiotic-resistant bacteria. Silver nitrate is a hemostatic, antiseptic and astringent. Silver zeolite is a form of antibacterial silver. Zeolite is a porous matrix of sodium aluminosilicate that can bind a large amount of silver ions within its micropores and throughout its surface. Ions are released from the zeolite matrix by exchange with other cations in solution and the amount released is proportional to the concentration of other cations in the solution. Minimum inhibitory concentration (MIC) silver zeolite ranges from 256 µg/ml to 2048 µg/ml, which corresponded to a range of 4.8 µg/ml to 38.4 µg/ml of Ag+.

Thallium: Thallium compounds such as thallium sulfate impregnated in wood or leather can kill fungal spores and bacteria, and for the protection of textiles from attack by moths. Thallium sulfate is a depilatory and can treatment venereal disease, skin fungal infections, and tuberculosis.

Tin: Tetrabutyltin is a disinfectant and also prevents slime formation in industrial recirculating water systems. Tricyclohexyltin hydroxide is an acaricide. Triphenyltin hydroxide and triphenyltin acetate are fungicides.

Zinc: Zinc oxide is a weak antiseptic and a mold-growth inhibitor. Zinc chloride is an ingredient in mouthwashes and deodorants, and zinc pyrithione is an ingredient in antidandruff shampoos. Galvanized (zinc-coated) fittings on roofs impede the growth of algae. Zinc iodide and zinc sulfate are topical antiseptics.

Example 1

A transparent thermoplastic urethane (TPU) film, polycaprolactone based aliphatic TPU resin having shore hardness of 60 D, was embedded with antimicrobial nanoparticles comprising NanoSeedz™ glass encapsulated ionic silver. Preferably the antimicrobial nanoparticles have a diameter of less than 10 nm. This film achieved 99.99% skill rate in 24 hours.

A polyethylene (PET) layer was adhered to this TPU film for rigidity and impact absorption. Additional polymer layers may also be added as described above for added functionality to the film.

Example 2

A top acrylic transparent polymer layer was embedded with antimicrobial nanoparticles comprising zeolite microporous aluminosilicate mineral retaining Ag, Cu and/or Zn metal ions. This top acrylic polymer layer is bonded to a layer of TPU, such as polycaprolactone based aliphatic TPU resin having shore hardness of 60 D, and the total resulting thickness of the bonded film is about 0.15 mm to 0.16 mm. Preferably the antimicrobial nanoparticles have a diameter of less than 10 nm. This film achieved a microbial kill rate of 99.99% in 8 hours. Additives were added to the top acrylic polymer layer, such as known agents that achieve UV protection against yellowing and haze and stain inhibitors. Optionally, the TPU layer may also be embedded with antimicrobial nanoparticles, including zeolite particles retaining Ag, Cu and/or Zn metal ions.

Specifications for this film are listed in Table 1 below.

TABLE 1

Specification of the film of Example 2.

| Description | Value |
| --- | --- |
| Transmittance | 100% via ASTMD 1003-13 |
| Haze | 2.81 via ASTMD 1003-13 |
| Shore A Durometer | 70 |
| Acrylic Crystallization | n/a |
| Anti-Glare | n/a |
| Master Role Width | 49" |
| Adhesive Type | Acrylic |
| Adhesive Backing Type/Thickness | Brushed PET/.05 mm |
| TPU Thickness | .15 mm |
| Antimicrobial Efficacy | 4 Log at 8 hour via JISZ 2801 |
| Antimicrobial Agent | Seal Sheild ZSZ2 |

An acrylic adhesive layer of 0.051 mm is added to the bottom of the bonded layer and a PET film is added for rigidity and impact absorption. The total thickness of the screen protector product is 0.3 mm. The screen protector product has a bottom adhesive layer of silicon, acrylic, or other adhesive for adhering the finished product to the substrate such as a touchscreen. A peel away PET layer is adhered to the bottom of the finished product to protect the adhesive layer.

In both cases, to achieve strength the antimicrobial film is bonded to, preferably, a PET layer. This product with PET layer is about 0.05 mm thick. The PET layer is excellent for energy or shock dissipation.

In both most cases, the bottom layer has an adhesive coating and a peel away polymer layer preferably comprises PET. The peel away polymer layer is used for wet or dry installation on a surface.

Although preferred embodiments of the invention have been described herein, it will be understood by those skilled in the art that variations may be made thereto without departing from the spirit of the invention or the scope of the appended claims. All documents disclosed herein, including those in the following reference list, are incorporated by reference.

REFERENCES

Der-Chi Tien, et al. Colloidal silver fabrication using the spark discharge system and its antimicrobial effect on *Staphylococcus aureus*. *Medical Engineering & Physics* Volume 30, Issue 8, Pages 948-952 (October 2008).

Der-Chi Tien, et al. Identification and quantification of ionic silver from colloidal silver prepared by electric spark discharge system and its antimicrobial potency study. *Journal of Alloys and Compounds*, Volume 473, Issues 1-2, Pages 298-302 (April 2009).

Juan Francisco Hernandez-Sierra, et al. The antimicrobial sensitivity of *Streptococcus mutans* to nanoparticles of silver, zinc oxide, and gold. *Nanomedicine: Nanotechnology, Biology and Medicine*, Volume 4, Issue 3, September 2008, Pages 237-240.

Amna Sirelkhatim, et al. Review on Zinc Oxide Nanoparticles: Antibacterial Activity and Toxicity Mechanism. *Nano-Micro Letters*, July 2015, Volume 7, Issue 3, pp 219-242.

T. N Kim, et al. Antimicrobial effects of metal ions (Ag+, Cu2+, Zn2+) in hydroxyapatite. *Journal of Materials Science: Materials in Medicine*, March 1998, Volume 9, Issue 3, pp 129-134.

Radhesh Kumar, et al. Silver ion release from antimicrobial polyamide/silver composites. *Biomaterials*, Volume 26, Issue 14, May 2005, Pages 2081-2088.

Shlomo Magdassi, et al. Ring Stain Effect at Room Temperature in Silver Nanoparticles Yields High Electrical Conductivity. *Langmuir*, 2005, 21 (23), pp 10264-10267.

Sukumaran Prabhu, et al. Silver nanoparticles: mechanism of antimicrobial action, synthesis, medical applications, and toxicity effects. *International Nano Letters*, December 2012, 2:32.

What is claimed is:

1. An antimicrobial transparent film comprising:
   a) polymer layer, comprising a polymer support matrix;
   b) antimicrobial nanoparticles evenly dispersed in the polymer support matrix, for providing a stored source of antimicrobial agents, the antimicrobial nanoparticles comprising:
      an ionic antimicrobial agent; and
      a support agent that localizes the ionic antimicrobial agent to external and/or internal surfaces of the support agent, and wherein the support agent releases the ionic antimicrobial agent through chemical exchange;
   wherein the polymer support matrix is cooperatively configured to allow the ionic antimicrobial agent released by the support agent to permeate or migrate through the polymer support matrix to a surface of the film, for maintaining an effective amount of antimicrobial agent on the surface of the film over a desired period of time to inhibit microbial growth and colonization; and
   wherein the polymer support matrix comprises a polycaprolactone based aliphatic TPU resin; and
   c) one or more additional layers bonded to the polymer layer, the one or more additional layers comprising an electronic or optical component embedded layer;
   wherein the electronic or optical component embedded layer comprises an electronic or optical component selected from the group comprising: capacitance measuring addressable electrodes, light or electrical conductive substances, Radio-frequency Identification (RFID) chips, Frustrated Total Internal Reflection (FTIR) systems, Ultra Violet (UV) light sensor, fingerprint or pattern identification sensors, and biological function sensors.

2. The antimicrobial transparent film of claim 1, comprising an adhesive layer disposed on a bottom surface of the polymer layer.

3. The antimicrobial transparent film of claim 1, wherein the antimicrobial nanoparticles are less than 100 nm in diameter.

4. The antimicrobial transparent film of claim 1, wherein the ionic antimicrobial agent is silver, zinc, or combinations thereof.

5. The antimicrobial transparent film of claim 1, wherein the support agent comprises a zeolite microporous aluminosilicate mineral.

6. The antimicrobial transparent film of claim 1, wherein the polymer support matrix comprises an acrylic polymer.

7. The antimicrobial transparent film of claim 1, wherein the antimicrobial nanoparticles are dispersed in the polymer layer with an average separation distance between each antimicrobial nanoparticles of at least greater than eight times the average diameter of the antimicrobial nanoparticles.

8. The antimicrobial transparent film of claim 1, wherein the antimicrobial nanoparticles are dispersed in the polymer support matrix with sufficient concentration to maintain an effective amount of antimicrobial agent on the surface of the film to exhibit 99.99% microbial kill rate in less than 24 hours, and wherein the antimicrobial transparent film has a haze of less than 10%.

9. The antimicrobial transparent film of claim 2, wherein the adhesive layer comprises a sodium silicate or an acrylic-based adhesive.

10. The antimicrobial transparent film of claim 1, wherein the one or more additional layers are selected from the group comprising: impact resistant layer, shock-absorbent layer, a rigidity layer, a vision enhancing layer, a privacy filter layer, an oxygen barrier layer, a water barrier layer, a chemical resistance layer, a UV degradation resistance layer, a photosensitive layer containing light-sensitive polychromatic molecules, and combinations thereof.

11. The antimicrobial transparent film of claim 10, comprising a surface electronic or optical component laminated on a top or bottom surface of the film or between the one or more additional layers.

12. The antimicrobial transparent film of claim 10, wherein one or more of the one or more additional layers comprise a polymer having antimicrobial nanoparticles dispersed in the polymer.

13. The antimicrobial transparent film of claim 12, wherein the polymer layer is a top layer, with an optional porous surface treatment.

14. The antimicrobial transparent film of claim 1, wherein the antimicrobial transparent film is a touch screen protector.

15. The antimicrobial transparent composition of claim 14, wherein the antimicrobial transparent composition has less than 7% haze.

16. The antimicrobial transparent composition of claim 15, wherein the antimicrobial transparent composition has less than 5% haze.

* * * * *